(12) United States Patent
Jespersen et al.

(10) Patent No.: US 10,264,783 B2
(45) Date of Patent: Apr. 23, 2019

(54) SPRAYABLE GELLING ANIMAL ATTRACTANT

(71) Applicant: Arcus Hunting, LLC, Covington, GA (US)

(72) Inventors: Mike Jespersen, Macon, GA (US); Grant Corbett, Macon, GA (US)

(73) Assignee: Arcus Hunting, LLC, Covington, GA (US)

(*) Notice: Subject to any disclaimer, the term of this patent is extended or adjusted under 35 U.S.C. 154(b) by 355 days.

(21) Appl. No.: 15/228,795

(22) Filed: Aug. 4, 2016

(65) Prior Publication Data

US 2018/0014531 A1  Jan. 18, 2018

Related U.S. Application Data

(60) Provisional application No. 62/362,439, filed on Jul. 14, 2016.

(51) Int. Cl.
| | | |
|---|---|---|
| *A01N 25/04* | (2006.01) | |
| *A01N 43/16* | (2006.01) | |
| *A01M 31/00* | (2006.01) | |
| *A01N 25/06* | (2006.01) | |
| *A01N 25/18* | (2006.01) | |

(52) U.S. Cl.
CPC .......... *A01N 25/04* (2013.01); *A01M 31/008* (2013.01); *A01N 25/06* (2013.01); *A01N 25/18* (2013.01); *A01N 43/16* (2013.01)

(58) Field of Classification Search
CPC ...... A01N 25/04; A01N 25/06; A01M 31/008
See application file for complete search history.

(56) References Cited

U.S. PATENT DOCUMENTS

| | | | | | |
|---|---|---|---|---|---|
| 5,474,030 | A | * | 12/1995 | Pittet | A01K 29/005 119/207 |
| 5,579,723 | A | * | 12/1996 | Pittet | A01K 29/005 119/207 |
| 2010/0137178 | A1 | * | 6/2010 | Smets | A61K 8/732 510/104 |
| 2010/0322990 | A1 | * | 12/2010 | Burke | A01N 25/04 424/405 |
| 2011/0146133 | A1 | * | 6/2011 | Bunker | A01M 1/02 43/132.1 |
| 2011/0184040 | A1 | * | 7/2011 | Taranta | A01N 25/00 514/427 |
| 2012/0282315 | A1 | * | 11/2012 | Tate | A01N 63/02 424/409 |
| 2015/0216182 | A1 | * | 8/2015 | Brown | A01N 57/16 424/405 |
| 2015/0272110 | A1 | * | 10/2015 | Lanter | A01M 31/008 426/1 |
| 2017/0251655 | A2 | * | 9/2017 | Frutos | A01M 1/103 |

* cited by examiner

*Primary Examiner* — Christopher P Ellis
(74) *Attorney, Agent, or Firm* — Hovey Williams LLP

(57) ABSTRACT

A gel-based and sprayable animal attractant composition is provided that comprises at least one synthetic scent. Generally, the gel-based animal attractant composition can be applied through the use of an aerosol spray can and can be formulated to attract specific types of animals, in particular ruminants. More specifically, the animal attractant can comprise a synthetic scent designed to mimic the urine of a doe in estrus.

14 Claims, 2 Drawing Sheets

SPRAYABLE GELLING ANIMAL ATTRACTANT

This application claims the benefit of U.S. Provisional Application Ser. No. 62/362,439, filed Jul. 14, 2016, entitled SPRAYABLE GELLING ANIMAL ATTRACTANT, which is hereby incorporated in its entirety by reference herein.

BACKGROUND

1. Field of the Invention

The present invention is generally related to animal attractants. More particularly, the present invention is generally related to sprayable ruminant attractants.

2. Description of the Related Art

Animal attractants have long been used by hunters to attract animals to hunt sites. Various types of animal attractants have been employed through the years, such as food-based attractants, water-based attractants, and scent-based attractants; however, scent-based attractants have become increasingly popular due to their versatility and ability to be applied to various substrates at a hunt site. Furthermore, scent-based attractants can be tailored to the specific game that the hunter is seeking and may be readily applied to multiple areas within a desired hunt site. In many cases, scent-based animal attractants can contain some natural scent derived from the desired game, such as urine, which can be used to attract the game to the hunt site.

Although scent-based animal attractants have become increasingly popular, such attractants can lose their potency and rapidly dissipate soon after application. Thus, there is still a need for a scent-based animal attractant that can maintain its potency for extended periods of time after application.

SUMMARY

One or more embodiments of the present invention concern a packaged animal attractant. The packaged animal attractant comprises: (a) an animal attractant composition; (b) a container to hold the animal attractant composition; and (c) a spraying mechanism operably connected to the container and configured to disperse the animal attractant composition. Furthermore, the animal attractant composition comprises: (i) a gelling agent and (ii) an animal scent concentrate comprising at least one synthetic animal scent selected from the group consisting of a phenol derivative, a diaryl ether, an indole derivative, an isochromene derivative, and mixtures thereof.

One or more embodiments of the present invention concern a method for applying a ruminant attractant composition in a ruminant habitat. Generally, the method comprises: (a) providing the ruminant attractant composition and (b) applying the ruminant attractant composition onto a substrate within the ruminant habitat. Furthermore, the ruminant attractant composition comprises an animal scent concentrate comprising at least one synthetic animal scent selected from the group consisting of a phenol derivative, a diaryl ether, an indole derivative, an isochromene derivative, and mixtures thereof. Furthermore, the ruminant attractant composition exhibits a viscosity at 25° C. and 1 atm of at least 3 cP and not more than 5,000 cP as measured using a Brookfield RV Viscometer.

One or more embodiments of the present invention concern a ruminant attractant composition. Generally, the ruminant attractant composition comprises: (i) a gelling agent and (ii) a ruminant scent concentrate comprising at least one synthetic animal scent selected from the group consisting of a phenol derivative, a diaryl ether, an indole derivative, an isochromene derivative, and mixtures thereof.

BRIEF DESCRIPTION OF THE FIGURES

Embodiments of the present invention are described herein with reference to the following drawing figures, wherein.

DETAILED DESCRIPTION

Figure 1:
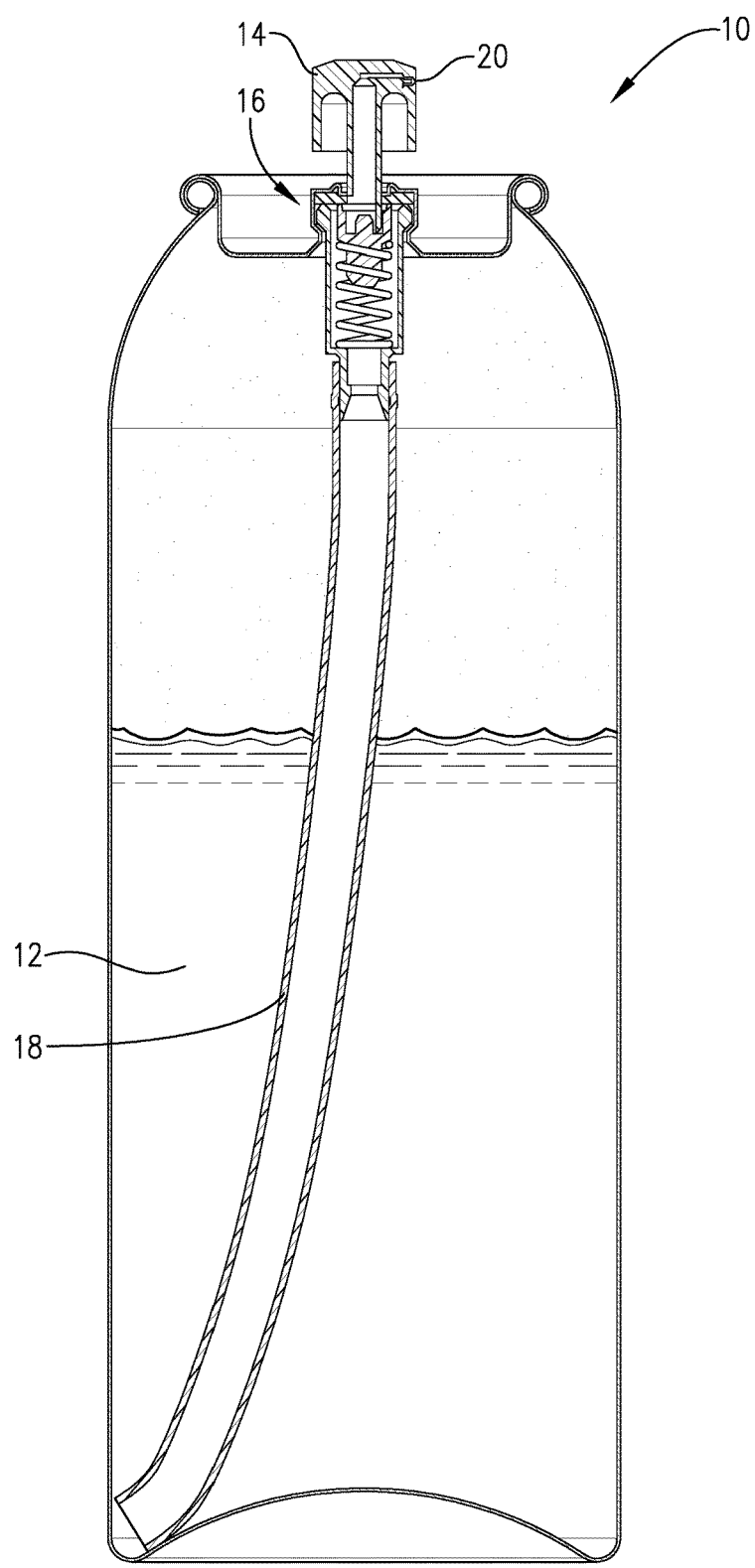
FIG. 1 provides a cross-sectional view of an aerosol spray can that may be used to apply the scent-based animal attractant of the present invention.

The present invention generally relates to scent-based animal attractants, especially scent-based attractants for ruminants. A "ruminant" is a mammal that has a four-compartment stomach and includes, for example, animals from the Cervidae family such as white-tailed deer, mule deer, red deer, reindeer, and fallow deer. Thus, in various embodiments, the animal attractant compositions and the animal scent concentrates described herein can be in the form of ruminant attractant compositions and ruminant scent concentrates, respectively.

Generally, the animal attractant compositions of the present invention can comprise an animal scent concentrate. These animal scent concentrates can comprise various scent-based compounds, which can be selected depending on the type of game one would want to attract. In various embodiments, these animal scent concentrates can be formulated to attract ruminants and may be referred to as "ruminant scent concentrates."

These ruminant scent concentrates can comprise any of the scent-based compounds described in the present invention. In various embodiments, the ruminant scent concentrates comprise at least one synthetic scent that mimics the smell of the urine from a ruminant. For example, the ruminant scent concentrate can comprise at least one synthetic scent that mimics the smell of doe estrus urine. As used herein, the term "synthetic" refers to any substance that was chemically synthesized and not naturally produced. Thus, synthetic fragrances and scents would not include any naturally-derived scents, such as urine or glandular extracts.

The various synthetic animal scents that can be used to form the animal scent concentrates are described in further detail below.

In one or more embodiments, the animal scent concentrate can comprise a phenol derivative such as, for example, p-cresol. For instance, the animal scent concentrate can comprise at least 0.5, 1, 5, 10, 15, 20, 25, 30, 35, 40, 45, or 50 weight percent of the phenol derivative and/or not more than 99, 95, 90, 85, 80, 75, 70, 65, 60, 55, or 50 weight percent of the phenol derivative. Generally, the phenol derivative can function as a synthetic fragrance that mimics certain animal scents, including scents generally associated with the urine of specific animals.

In one or more embodiments, the animal scent concentrate can comprise a diaryl ether such as, for example, diphenyl ether. For instance, the animal scent concentrate can comprise at least 0.001, 0.01, 0.05, or 0.1 weight percent of the diaryl ether and/or not more than 25, 20, 15, 10, 5, or 2.5 weight percent of the diaryl ether. The diaryl ether can also function as a synthetic fragrance that mimics certain animal scents.

In one or more embodiments, the animal scent concentrate can comprise an indole derivative such as, for example, 3-methylindole, which can also be referred to as skatole. For instance, the animal scent concentrate can comprise at least 0.01, 0.05, 0.1, 0.5, or 1 weight percent of the indole derivative and/or not more than 25, 20, 15, 10, 5, or 2.5 weight percent of the indole derivative. The indole derivative can function as a fragrance and/or a fixative in the animal scent concentrate. In certain embodiments, the indole derivative can mimic certain scents found in animal excreta (e.g., urine or fecal matter).

In one or more embodiments, the animal scent concentrate can comprise an isochromene derivative such as, for example, galaxolide. For instance, the animal scent concentrate can comprise at least 0.001, 0.005, 0.01, 0.05, or 0.1 weight percent of the isochromene derivative and/or not more than 25, 20, 15, 10, 5, 2.5, or 1 weight percent of the isochromene derivative. In certain embodiments, the isochromene derivative can mimic scents generally associated with certain glandular-based scents of animals (e.g., musk).

In various embodiments, the animal scent concentrate comprises at least one synthetic animal scent selected from the group consisting of a phenol derivative, a diaryl ether, an indole derivative, an isochromene derivative, and mixtures thereof. In one or more embodiments, the animal scent concentrate comprises at least two or three synthetic animal scents selected from the group consisting of a phenol derivative, a diaryl ether, an indole derivative, and an isochromene derivative. In certain embodiments, the animal scent concentrate comprises a phenol derivative, a diaryl ether, an indole derivative, and an isochromene derivative.

In addition to the aforementioned synthetic scents, the animal scent concentrate can comprise various other components.

In one or more embodiments, the animal scent concentrate can comprise a benzyl derivative. The benzyl derivative can comprise benzyl benzoate, benzyl alcohol, or a mixture thereof. For example, the animal scent concentrate can comprise at least 0.5, 1, 5, or 10 weight percent of the benzyl derivative and/or not more than 75, 60, 50, 40, 35, 30, or 25 weight percent of the benzyl derivative. Generally, the benzyl derivative can serve multiple functions in the animal scent concentrate and can function as a solvent, a stabilizer, and/or a preservative in the concentrate.

In one or more embodiments, the animal scent concentrate can comprise a phthalate derivative such as, for example, a diethyl phthalate. For example, the animal scent concentrate can comprise at least 0.5, 1, 5, or 10 weight percent of the phthalate derivative and/or not more than 75, 60, 50, 40, 35, 30, or 25 weight percent of the phthalate derivative. Generally, the phthalate derivative can function as a plasticizer and facilitate the application of the concentrate when added to the animal attractant composition of the present invention.

In one or more embodiments, the animal scent concentrate can comprise 2-phenylethanol, which can function as a preservative in the concentrate. For example, the animal scent concentrate can comprise at least 0.001, 0.01, 0.05, or 0.1 weight percent of the 2-phenylethanol and/or not more than 25, 20, 15, 10, 5, or 2.5 weight percent of the 2-phenylethanol.

In one or more embodiments, the animal scent concentrate can comprise coumarin. For example, the animal scent concentrate can comprise at least 0.001, 0.01, 0.05, or 0.1 weight percent of the coumarin and/or not more than 25, 20, 15, 10, 5, or 2.5 weight percent of the coumarin. Generally, the coumarin can function as a synthetic scent that enhances the aroma of the concentrate.

In one or more embodiments, the animal scent concentrate can comprise 2'-acetonaphthone. For example, the animal scent concentrate can comprise at least 0.001, 0.01, 0.05, or 0.1 weight percent of the 2'-acetonaphthone and/or not more than 25, 20, 15, 10, 5, or 2.5 weight percent of the 2'-acetonaphthone. Generally, the 2'-acetonaphthone can function as a fragrance or preservative in the concentrate.

In one or more embodiments, the animal scent concentrate can comprise an anthranilic acid derivative such as, for instance, methyl anthranilate. For example, the animal scent concentrate can comprise at least 0.001, 0.005, 0.01, 0.05, or 0.1 weight percent of the anthranilic acid derivative and/or not more than 25, 20, 15, 10, 5, 2.5, or 1 weight percent of the anthranilic acid derivative. Generally, the anthranilic acid derivative can function as a synthetic scent that enhances the aroma of the concentrate.

In one or more embodiments, the animal scent concentrate can comprise a limonene derivative. For example, the animal scent concentrate can comprise at least 0.001, 0.005, 0.01, 0.05, or 0.1 weight percent of the limonene derivative and/or not more than 25, 20, 15, 10, 5, 2.5, or 1 weight percent of the limonene derivative. Generally, the limonene derivative can function as a synthetic scent that enhances the aroma of the concentrate.

In addition to the aforementioned synthetic scents, the animal scent concentrate can comprise at least one natural fragrance such as, for example, actual urine from the animal of interest. For instance, the animal scent concentrate could comprise urine from a white-tailed doe in estrus. In one or more embodiments, the animal scent concentrate and/or the animal attractant composition can comprise less than 10, 5, 1, 0.1, or 0.01 weight percent of a natural fragrance derived from an animal, such as urine. In certain embodiments, the animal scent concentrate and/or the animal attractant composition can comprise no natural fragrances derived from an animal, such as urine.

In addition to containing scents designed to attract specific animals, the animal scent concentrates may also comprise one or more animal repellants for repelling an undesirable animal, such as a predator to the desired game species. For instance, the animal scent concentrate could comprise a bear repellant since bears are a natural predator for certain ruminants.

As discussed above, the animal scent concentrates described herein can be combined with various other components to form the animal attractant compositions of the present invention. In various embodiments, the animal attractant compositions can comprise at least 0.5, 1, 2, 5, 6, 7, 8, 9, or 10 weight percent of the animal scent concentrate and/or not more than 90, 75, 60, 50, 40, 30, 25, 20, or 15 weight percent of the animal scent concentrate.

Unlike previous animal attractants, the animal attractant compositions of the present invention can maintain its fragrant potency well after its application, which is partly due to the gelling agent added to the composition. As previously noted, the animal attractant compositions described herein can comprise at least one gelling agent. As used herein, a "gelling agent" refers to a compound that is capable of increasing the viscosity of the animal attractant composition. In one or more embodiments, the gelling agent can comprise a synthetic clay, a cellulose derivative, or a mixture thereof. For instance, the cellulose derivative can comprise hypromellose and the synthetic clay can comprise laponite. In other embodiments, the gelling agent can comprise an organogel, a xerogel, or a mixture thereof.

In various embodiments, the animal attractant composition can comprise at least 0.5, 1, 2, 3, 4, or 5 weight percent of at least one gelling agent and/or not more than 90, 75, 60, 50, 40, 30, 25, 20, 15, or 10 weight percent of at least one gelling agent.

Due to the gelling agent, the animal attractant compositions may have a viscosity at 25° C. and 1 atm of at least 1, 3, 5, 10, 50, 100, or 250 cP and/or not more than 5,000, 4,000, 3,000, 2,000, 1,000, or 500 cP as measured using a Brookfield RV Viscometer. Additionally or alternatively, the animal attractant compositions may have a viscosity at 25° C. and 1 atm of at least 1, 3, 5, 10, 50, 100, or 250 cP and/or not more than 5,000, 4,000, 3,000, 2,000, 1,000, or 500 cP as measured using a Brookfield RV Viscometer after being applied (e.g., sprayed) onto a substrate and allowed to rest for 10 minutes at 25° C.

Moreover, the animal attractant compositions can comprise at least one solvent such as, for example, an alcohol, a benzyl derivative, or a mixture thereof. In certain embodiments, the alcohol can be ethanol and the benzyl derivative can be benzyl benzoate. In various embodiments, the animal attractant composition can comprise at least 5, 10, 15, 20, 25, 30, 35, 40, 45, or 50 weight percent of the solvent and/or not more than 99, 95, 90, 85, or 84 weight percent of the solvent.

Furthermore, the animal attractant composition can comprise various additives and other fillers. Such additives can include, for example, a petroleum-based gas. For instance, the animal attractant composition can comprise at least 1, 5, 10, or 14 weight percent of the petroleum gas and/or not more than 90, 70, 50, 30, or 25 weight percent of the petroleum gas.

The animal attractant compositions can be formed by mixing the animal scent concentrate and any other ingredients utilizing conventional mixers known in the art, especially the fragrance industry. Thus, the animal attractant compositions can be formed by any method commonly used in the art to produce fragrances.

Generally, the animal attractant compositions can be packaged and stored in a container, which can be any conventional container used in the art. In one or more embodiments, the container comprises a pressurized spray can or a spray bottle. In certain embodiments, the container can be an aerosol spray can. In such embodiments, the container can also contain a pressurized propellant such as isobutene, propane, or a mixture thereof.

Pressurized aerosol-based containers that can be used to disperse the animal attractant compositions are described in further detail in U.S. Pat. No. 8,206,697, which is incorporated by reference in its entirety.

Furthermore, in various embodiments, the container can also contain a spraying mechanism operably connected to the container and configured to disperse the animal attractant composition. Such spraying mechanism can comprise any mechanism known in the art capable of dispersing a gelled animal attractant. In one or more embodiments, the spraying mechanism comprises an aerosol spray mechanism. In certain embodiments, the spraying mechanism comprises a 360 degree valve assembly that allows the contents of the container to be sprayed in any direction.

An exemplary aerosol can 10 for the present invention is depicted in FIG. 1. As shown in FIG. 1, the aerosol can 10 can hold the animal attractant composition 12 under pressure. When one would want to disperse the animal attractant composition 12 from the can 10, they would apply pressure onto the actuator 14, which will then cause the composition to be taken up by the valve assembly 16 through the dip tube 18. The composition will then be dispersed through the outlet 20 of the spraying mechanism.

In one or more embodiments, the container comprises a pressurized aerosol spray can, which disperses the animal attractant composition in the form of stream and not as an atomized mist. Thus, in such embodiments, a user is able to apply the animal attractant composition with pinpoint accuracy, thereby allowing the user to apply the composition from a distance and minimize the possibility of contaminating the application area with their personal scents. For example, the animal attractant composition can be dispersed in the form of a tight stream. Such a tight stream can be characterized by the fact that at least 50, 75, or 90 weight percent of the stream would pass through a circular opening having a diameter of 1 inch when the circular opening is spaced 1, 2, 4, 6, or 8 feet from the spraying outlet of the aerosol spray can.

When utilizing the animal attractant compositions in a container with a spraying mechanism, the animal attractant compositions can be applied to any desired surface. Generally, these surfaces can be in the habitat of the desired game animal. In various embodiments, the animal attractant composition can be applied to a surface within the habitat of a ruminant. These surfaces can be any natural or artificial surface found within the habitat of the animal. Exemplary natural surfaces include the surfaces of rocks, plants, and trees, while exemplary artificial surfaces include the surfaces of a hunting blind, tent, and clothes.

Figure 2:
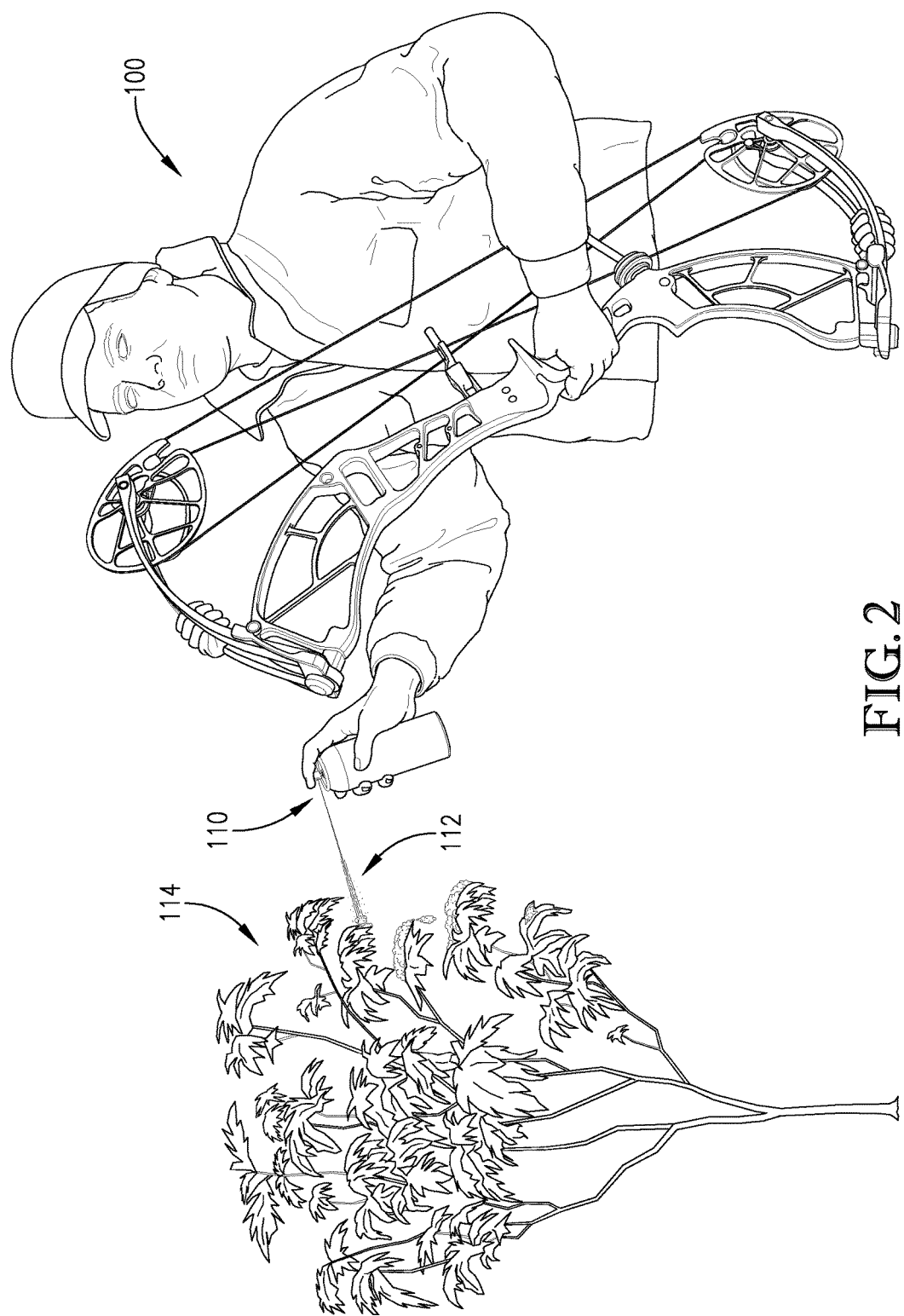
FIG. 2 demonstrates a hunter applying the scent-based animal attractant of the present invention on a plant.

FIG. 2 depicts a hunter 100 using an aerosol can 110 to apply a stream of the animal attractant composition 112 onto a plant 114 within a ruminant habitat.

Due to the gelling agents, the applied animal attractant compositions can maintain their potency and weight well after being applied onto a substrate. For example, the animal attractant compositions can exhibit an evaporation rate of less than 50, 25, or 10 weight percent after 1 hour, 6 hours, or 12 hours at 25° C. As used herein, "evaporation rate" compares the difference in weight of the initially-applied animal attractant composition and the same composition at a later time interval.

In alternative embodiments, the animal attractant compositions can be pre-applied on a disposable substrate to form a scented substrate, which can then be packaged and sold. Exemplary disposable substrates can include wicks, scent pads, cotton balls, cotton rolls, wafers, or any other disposable substrate capable of absorbing the animal attractant composition and permitting the scents therefrom to be released into the environment. The scented substrates can be removed from the packaging to thereby expose the scents from the animal attractant composition to the environment.

The preferred forms of the invention described above are to be used as illustration only, and should not be used in a limiting sense to interpret the scope of the present invention. Modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as it pertains to any apparatus not materially departing from but outside the literal scope of the invention as set forth in the following claims.

DEFINITIONS

It should be understood that the following is not intended to be an exclusive list of defined terms. Other definitions may be provided in the foregoing description, such as, for example, when accompanying the use of a defined term in context.

As used herein, the terms "a," "an," and "the" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," and "have" have the same open-ended meaning as "comprising," "comprises," and "comprise" provided above.

As used herein, the terms "including," "include," and "included" have the same open-ended meaning as "comprising," "comprises," and "comprise" provided above.

NUMERICAL RANGES

The present description uses numerical ranges to quantify certain parameters relating to the invention. It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting "greater than 10" (with no upper bounds) and a claim reciting "less than 100" (with no lower bounds).

What is claimed is:

1. A method for applying a ruminant attractant composition in a ruminant habitat, wherein said method comprises:
   (a) providing said ruminant attractant composition, wherein said ruminant attractant composition comprises an animal scent concentrate comprising at least one synthetic animal scent selected from the group consisting of a phenol derivative, a diaryl ether, an indole derivative, an isochromene derivative, and mixtures thereof, wherein said ruminant attractant composition exhibits a viscosity at 25° C. and 1 atm of at least 3 cP and not more than 5,000 cP as measured using a Brookfield RV Viscometer; and
   (b) applying said ruminant attractant composition onto a substrate within said ruminant habitat.

2. The method of claim 1, wherein said applying of step (b) comprises spraying a stream of said ruminant attractant composition from a spraying mechanism onto said substrate, wherein said stream is characterized by the fact that at least 90 weight percent of said stream would pass through a circular opening having a diameter of 1 inch when said circular opening is spaced 1 foot from the outlet of said spraying mechanism.

3. The method of claim 1, wherein said ruminant attractant composition comprises:
   (i) at least 2 weight percent of the animal scent concentrate; and
   (ii) at least 1 weight percent of a gelling agent.

4. The method of claim 1, wherein said animal attractant composition exhibits an evaporation rate of less than 50 weight percent after 1 hour at 25° C.

5. The method of claim 1, wherein said animal scent concentrate comprises at least two synthetic animal scents selected from the group consisting of a phenol derivative, a diaryl ether, an indole derivative, and an isochromene derivative.

6. The method of claim 1, wherein said animal scent concentrate comprises at least three synthetic animal scents selected from the group consisting of a phenol derivative, a diaryl ether, an indole derivative, and an isochromene derivative.

7. The method of claim 1, wherein the animal scent concentrate comprises said indole derivative, wherein said indole derivative comprises 3-methylindole.

8. The method of claim 1, wherein the animal scent concentrate comprises said isochromene derivative, wherein said isochromene derivative comprises galaxolide.

9. A ruminant attractant composition, wherein said ruminant attractant composition comprises:
   (a) a gelling agent, and
   (b) a ruminant scent concentrate comprising at least one synthetic animal scent selected from the group consisting of a phenol derivative, a diaryl ether, an indole derivative, an isochromene derivative, and mixtures thereof, wherein said ruminant attractant composition exhibits a viscosity at 25° C. and 1 atm of at least 3 cP and not more than 5,000 cP as measured using a Brookfield RV Viscometer.

10. The ruminant attractant composition of claim 9, wherein said ruminant attractant composition comprises:
    (i) at least 2 weight percent of the animal scent concentrate; and
    (ii) at least 1 weight percent of the gelling agent.

11. The ruminant attractant composition of claim 9, wherein said ruminant scent concentrate comprises at least two synthetic animal scents selected from the group consisting of a phenol derivative, a diaryl ether, an indole derivative, and an isochromene derivative.

12. The ruminant attractant composition of claim 9, wherein said ruminant scent concentrate comprises at least three synthetic animal scents selected from the group consisting of a phenol derivative, a diaryl ether, an indole derivative, and an isochromene derivative.

13. The ruminant attractant composition of claim 9, wherein said ruminant scent concentrate comprises said phenol derivative and said indole derivative, wherein said phenol derivative comprises p-cresol and said indole derivative comprises 3-methylindole.

14. The ruminant attractant composition of claim 9, wherein said ruminant scent concentrate comprises said isochromene derivative, wherein said isochromene derivative comprises galaxolide.

* * * * *